United States Patent
Slepian

(10) Patent No.: US 10,478,404 B2
(45) Date of Patent: Nov. 19, 2019

(54) MATERIALS, METHODS AND DEVICES FOR ALTERING CELL REACTIVITY

(71) Applicant: The Arizona Board of Regents on behalf of The University of Arizona, Tucson, AZ (US)

(72) Inventor: Marvin J. Slepian, Tucson, AZ (US)

(73) Assignee: Arizona Board of Regents on behalf of the University of Arizona, Tucson, AZ (US)

(*) Notice: Subject to any disclaimer, the term of this patent is extended or adjusted under 35 U.S.C. 154(b) by 0 days.

(21) Appl. No.: 15/113,393

(22) PCT Filed: Jan. 26, 2015

(86) PCT No.: PCT/US2015/012960
§ 371 (c)(1),
(2) Date: Jul. 21, 2016

(87) PCT Pub. No.: WO2015/113001
PCT Pub. Date: Jul. 30, 2015

(65) Prior Publication Data
US 2017/0007552 A1     Jan. 12, 2017

Related U.S. Application Data

(60) Provisional application No. 61/931,398, filed on Jan. 24, 2014.

(51) Int. Cl.
| | | |
|---|---|---|
| *A61K 31/137* | (2006.01) | |
| *A61K 31/138* | (2006.01) | |
| *A61K 31/185* | (2006.01) | |
| *A61K 31/44* | (2006.01) | |
| *A61M 1/12* | (2006.01) | |
| *A61K 31/10* | (2006.01) | |
| *A61K 31/165* | (2006.01) | |
| *A61K 31/202* | (2006.01) | |
| *A61K 35/19* | (2015.01) | |
| *C12N 5/00* | (2006.01) | |
| *C12N 5/078* | (2010.01) | |
| *A61K 31/337* | (2006.01) | |
| *A61K 31/575* | (2006.01) | |
| *A61K 31/685* | (2006.01) | |
| *A61K 31/407* | (2006.01) | |
| *A61M 1/10* | (2006.01) | |

(52) U.S. Cl.
CPC .......... *A61K 31/10* (2013.01); *A61K 31/165* (2013.01); *A61K 31/202* (2013.01); *A61K 31/337* (2013.01); *A61K 31/407* (2013.01); *A61K 31/575* (2013.01); *A61K 31/685* (2013.01); *A61K 35/19* (2013.01); *A61M 1/10* (2013.01); *C12N 5/0006* (2013.01); *C12N 5/0644* (2013.01); *C12N 2500/36* (2013.01); *C12N 2500/62* (2013.01)

(58) Field of Classification Search
CPC .. A61K 31/165; A61K 31/137; A61K 31/138; A61K 31/185; A61K 31/44; A61M 1/10; A61M 1/122; A61M 1/125; C12N 5/0634; C12N 5/0006
See application file for complete search history.

(56) References Cited

U.S. PATENT DOCUMENTS

2002/0032149 A1* 3/2002 Kensey ............. A61B 5/02028
514/1

FOREIGN PATENT DOCUMENTS

| EP | 0684762 | 8/1998 |
|---|---|---|
| WO | 00069429 | 11/2000 |
| WO | 2003085400 | 10/2003 |
| WO | 2003094915 | 11/2003 |
| WO | 2005113006 | 12/2005 |
| WO | 2007005180 | 4/2007 |

OTHER PUBLICATIONS

Hu et al., Am. J. Physiol. 277 (Heart Circ. Physiol. 46), H1593-99 (1999).*
Chasis et al., Blood 74(3), 1112-20 (1989).*
Greve et al., Am. J. Physiol. Heart Circ. Physiol. 291: H1700-08, 2006.*
Argenziano et al., "A prospective randomized trial of arginine vasopressin in the treatment of vasodilatory shock after left ventricular assist device placement," Circulation Nov. 4, 1997; 96(9 Suppl): II-286-90. PMID: 9386112. (Year: 1997).*
Bershadsky, et al., "Adhesion-mediated mechanosensitivity: a time to experiment, and a time to theorize," Curr Opin Cell Biol., 18:472-81 (2006).
Du, et al., "Grafted poly-(ethylene glycol) on lipid surfaces inhibits protein adsorption and cell adhesion," Biochem Biophys Acta., 1326(2):236-48 (1997).
Geiger, et al., "Assembly and mechanosensory function of focal contacts," Curr Opin Cell Biol., 13:584-92 (2001).
Geiger, et al., "Exploring the neighborhood: adhesion-coupled cell mechanosensors," Cell, 110:139-42 (2002).
Girdhar, et al., "Device thrombogenicity emulation: a novel method for optimizing mechanical circulatory support device thromboresistance," PLOS One, 7(3):e32463 (2012).

(Continued)

*Primary Examiner* — Theodore R. West
(74) *Attorney, Agent, or Firm* — Pabst Patent Group LLP

(57) ABSTRACT

Methods, compositions, and devices to limit, modulate, insulate, and/or otherwise alter the effects of exogenous physical stimuli on cells are described herein. The cells may be removed from the body, preferably isolated, and treated ex vivo with the composition to limit the effects of physical stimuli on the cells and then returned to the patient. Alternatively, the cells may be treated in vivo. The compositions can be administered a variety of manners, such as systemically, locally or regionally.

16 Claims, 8 Drawing Sheets

(56) References Cited

OTHER PUBLICATIONS

Gurbel, et al., "Evaluation of platelets in heart failure: Is platelet activity related to etiology, functional class, or clinical outcomes," Am Heart J., 143(6):1068-75 (2002).
Hornsey, Freezing of buffy coat-derived leukoreduced platelet concentrates in 6 percent dimethyl sulfoxide, Transfusion, 48(12):2508-14 (2008).
International Search Report for PCT/US2015/012960 dated Apr. 1, 2015.
Khurama, et al., "Monitoring platelet glycoprotein IIb/IIIa-fibrin interaction with tissue factor-activated thromboelastography," J Lab Clin Med., 138(4):401-11 (1997).
Lee, et al., "Water channels in platelet volume regulation," J Cell Mol Med, 16:945-9 (2012).
Lucitt, et al., "Assaying the efficacy of dual-antiplatelet therapy: use of a controlled-shear-rate microfluidic device with a well-defined collagen surface to track dynamic collagen surface to track dynamic platelet adhesion," Anal Bioanal Chem., 405(14):4823-34 (2013).
Marsh, et al., "Lipid membranes with grafted polymers: physicochemical aspects," Biochem Biophys Acta., 1615(1-2):33-59, (2003).
Pothapragada, et al., "A phenomenological particle-based platelet model for simulating filopodia formation during early activation," Intl J Numer Meth Biomed Eng., DOI:10.1002/cnm.2702 (2014).
Saniabadi, et al., "Effect of dipyridamole alone and in combination with aspirin on whole blood platelet aggregation, PG12 generation, and red cell deformability ex vivo in man," Cardiov Res., 25:177-83 (1991).
Serebruany, et al., "Clinical utility of the platelet function analyzer (PFA-100) for the assessment of the platelet status in patients with congestive heart failure (EPCOT trial)," Thrombosis Res., 101(6);427-33 (2001a).
Serebruany, et al., "Dipyridamole decreases protease-activated receptor and annexin-v binding on platelets of poststroke patients with aspirin nonresponsiveness," Cerebrov Diseases, 21(1-2):98-105 (2006).
Serebruany, et al., "Uniform platelet activation exists before coronary stent implantation despite aspirin therapy," Am Heart J., 142(4):611-6 (2001b).
Sheriff, et al., "Comparative efficacy of in vitro and in vivo metabolized aspirin in the DeBakey ventricular assist device," J Thromb Throbol., 37(4):499-506 (2014).
Sheriff, et al., "Evaluation of shear-induced platelet activation models under constant and dynamic shear stress loading conditions relevant to devices:," Ann Biomed Eng., 41(6):1279-96 (2013).
Sheikh, et al., "Treatment of neutrophils with cytochalasins converts rolling to stationary adhesion on P-selectin," J Cell Physiology, 174(2):206-16 (1998).
Soares, et al., "Simulation of platelets suspension flowing through a stenosis model using a dissipative particle dynamics approach," Ann Biomed Eng., 41(11):2318-33 (2013).
Xenos, et al., "Device thrombogenicity emulator (CTE)—Design optimization methodology for cardiovascular devices: A study in two bileaflet MHV designs," J Biomechanics, 742(12):2400-09 (2010).
Zaidel-Bar, et al., "Hierarchical assembly of cell-matrix adhesion complexes," Biochem Soc Trans., 32(pt2):416-20 (2004).
Zhang, et al., "Multiscale particle-based modeling of flowing platelets in blood plasma using dissipative particle dynamics and coarse grained molecular dynamics," Cell Mole Bioeng., 7(4):552-74 (2014).
Wehrle-Haller, et al., Trends in Cell Biology, 12(8):382-9 (2002).

* cited by examiner

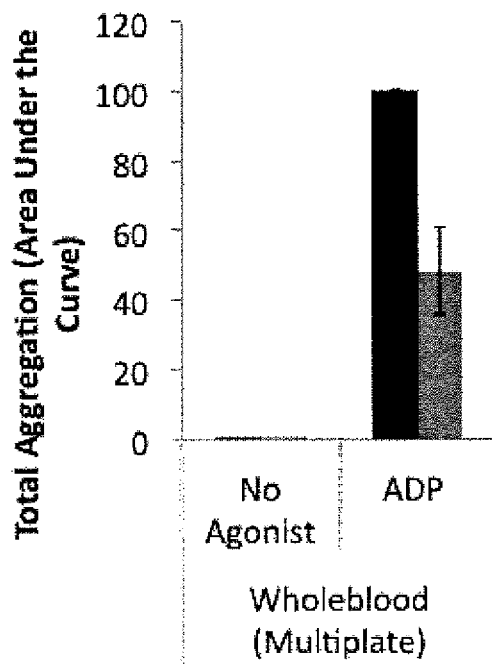
FIG. 2A
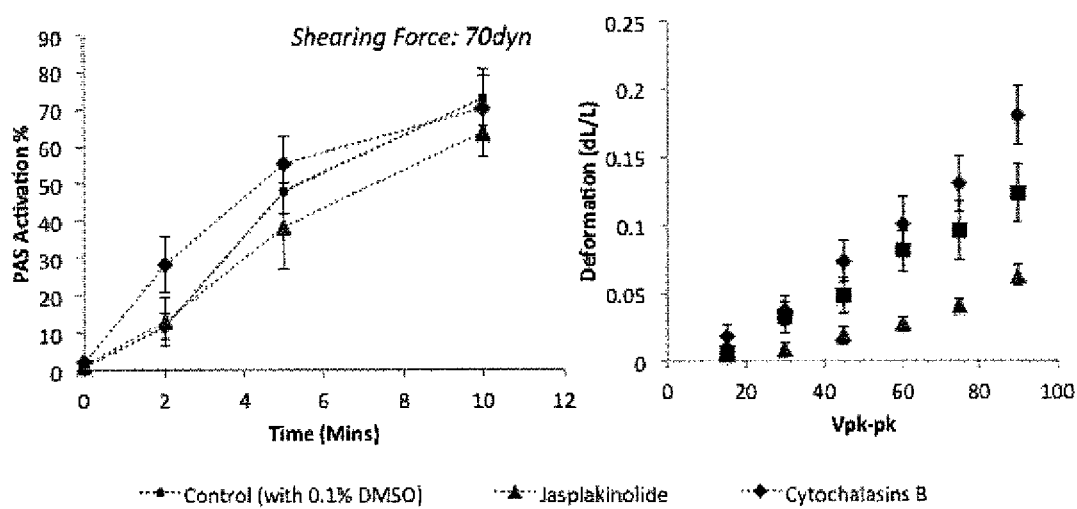
FIG. 2B
FIG. 2C

MATERIALS, METHODS AND DEVICES FOR ALTERING CELL REACTIVITY

CROSS-REFERENCE TO RELATED APPLICATIONS

This application is a 371 application of International Application No. PCT/US2015/012960 filed Jan. 26, 2015, which claims benefit of U.S. Provisional Application No. 61/931,398, filed Jan. 24, 2014.

STATEMENT REGARDING FEDERALLY SPONSORED RESEARCH

This invention was made with government support under Grant U01 EB012487 awarded by NIH. The government has certain rights in the invention.

FIELD OF THE INVENTION

The invention is generally directed to agents or compositions that alter cell reactivity, most notably to exogenous physical forces, e.g. shear forces, and methods of use thereof.

BACKGROUND OF THE INVENTION

Cells, the common building blocks of life, from the single cell to the multi-cellular organism remain functionally intact by virtue of their surrounding envelope. For all cells this is the cell membrane. For specialized cells, i.e. plant cells, this includes a cell wall. To operate in the larger environment cells communicate across the cell membrane, bringing in nutrients, dissolved gases, stimulating biochemicals, signaling molecules, hormones and other ionic or molecular entities involved in function, which may be normal or modified based on these stimuli. Similarly, cells exchange and export numerous compounds which are used for communication, either in the local environment (autocrine and paracrine functions) as well as in the larger environment, i.e. endocrine function or beyond. So the essential element here is the intactness, normality as well as selective function of the cell membrane.

In addition to chemical and biochemical stimuli cells respond to physical stimuli. Application of pressure, electrical fields, magnetic fields, light and other electromagnetic radiation, ultrasound, audible sound and beyond, frictional forces, heat, cold or shear forces may all modulate cell function.

The mechanism by which physical forces, in particular shear forces, tractional forces, frictional forces, and pressure, are sensed by the cell involves a complex set of cellular components via a process referred to as mechano-transduction. Briefly, a series of cell surface receptors, most notably integrins, hetero-dimeric protein receptors made of two subunits, alpha and beta, come together to form a functional receptor. These receptors typically interact with surrounding extracellular matrix proteins and physical substrates.

Integrins represent a complex family with over 18 alpha subunits and 8 beta subunits, which come together to form varying combinations, with a range of specificity to defined matrix proteins. For example, alpha1 beta1 and alpha 2 beta 1 typically bind to collagen. Alpha 5 beta-1 more typically binds to fibronectin, alpha V beta 3 has been referred to as the Vitronectin receptor. While elements of specificity exist for specific combinations of integrin subunit pairs, a variable degree of promiscuity exists in integrin-ligand interaction, to provide for redundancy and adhesion. Beyond the adhesive function of integrin receptors, these moieties sit in the membrane like antennae and respond to shear, tugging, and physical manipulation to "transmit" the physical stimuli through the membrane to sub-membrane assemblies.

These sub-membrane assemblies contain protein complexes, which include FAK kinase and other kinases, talin, paxillin and vinculin, all of which function to phosphorylate a cascade of proteins, which then signal, trigger and modulate intra-cellular processes. Such processes may include modulation of protein function, i.e., post-translational modification, induction of protein synthesis or alteration of gene expression. On the physical side integrin-ligand signaling may stimulate intracellular micro filaments, which run throughout the cell like "guywires," altering cell shape, stimulating cell membrane alteration, sending out cell projections or budding of vesicles. Additionally, microtubules may be stimulated, which act both as physical structural devices as well as transport systems to similarly evoke intra-cellular processes.

A link exists between integrins and the cell membrane. Integrins reside within cell membranes; thus, their positioning, stabilization and grounding within the membrane is essential for normal function in order to transduce mechanical and other physical stimuli.

By analogy, integrins may be viewed as basic pillars or posts within a cell membrane "foundation." Pillars and posts in the building must be structurally intact to provide support and communication between the building and the underground, so as to provide structural rigidity and stability. If the foundation, i.e. the membrane, in which they reside is shaky, loose or fluid the functional effect, stability in the case of this analogy, is diminished or completely lost. This also applies to integrins and cell membranes. If the cell membrane function is altered due to physical forces, chemical activity or other exogenous stimuli, transduction of information from both the "outside-in," as well as the "inside-out" may be altered.

Beyond integrin-mediated mechano-transduction, other means of transmitting exogenous physical stimuli into the cell, to alter function, exist. This may occur via perturbation of numerous cell surface receptors as well. These receptors include cadherins, immunoglobulin superfamily, gangliosides, selectins, syndecans and the like.

Further, stimulation may occur via nonspecific membrane damage creating pores, rifts, rents, or other physical communication means allowing contact and mixing of the extracellular and intracellular environments.

A need exists therefore to protect cells from harmful external physical stimuli, to stabilize membrane function so as to limit membrane damage as well as maintain normal integrin function and avoid inappropriate or non-specific mechano-transductive signaling when cells are subjected to exogenous physical stimuli, most notably shear forces, and to otherwise insulate cells to control cell function.

A major disease affecting man today is congestive heart failure. Heart failure is the final common pathway of all forms of heart disease. Whether one is afflicted with atherosclerotic coronary artery disease leading to reduced blood flow in coronary vessels; or one has a myopathy in which the cardiac muscle pumps poorly; or suffers from an arrhythmia where cardiac contraction is cacophonous; or has a narrowed (stenotic) or insufficient valve, at the end of the day heart pump function is compromised. This is known as heart failure. While we have made major advances in the treatment of heart failure through the use of pharmacologic agents such as ACE inhibitors, beta blockers, digoxin and diuretics, as heart function declines one eventually needs augmentation or replacement of pump function. This need has led in recent years to the advance of a new field known as mechanical circulatory support or MCS. In MCS a series of pump devices including ventricular assist devices (VADs) as well as the total artificial heart have been developed. While these devices are effective in either augmenting or supplanting cardiac function, at the same time they subject blood cells to significant exogenous physical forces. The most extreme example of this phenomenon occurs with ventricular assist devices.

As blood traverses and is propelled through a VAD, significant shear forces are imparted to the cells. In the beginning of the MCS era, devices were largely pulsatile, subjecting cells to shear and turbulence at a level above physiologic shear (i.e. >0-50 dynes/cm$^2$) though typically in ranges only slightly above physiologic levels. A new class of VAD was developed, that of a continuous flow rotary or centrifugal blood pump. These devices are akin to a small "jet engine" being placed within the bloodstream. They spin at ranges of 7000 to 12,000 rpm or beyond and impart shear in the 100's if not 1000's of dynes/cm$^2$. As such platelets, red blood cells and white cells subjected to these extreme forces undergo physical stimulation via both mechano-transductive mechanisms as well as direct force interaction leading to both biochemical and physical stimulatory events. In the extreme, these forces may lead to membrane fragmentation, resulting in direct communication between the extracellular and intracellular environment, or frank disruption of these cells leading to spillage of intracellular contents and exposure of cell membranes in the bloodstream. In the blood environment this can have dire if not fatal consequences.

This type of stimulation of platelets, (as well as RBCs and WBCs) instantly and dramatically drives thrombosis. If the level of damage and the number of cells stimulated is significant enough both local and distant thrombus formation may occur. This can lead to reduction of VAD pump function and potential death of the patient due to reduced cardiac output. More commonly thrombus formation may propagate, break off, embolize, or be showered distally via the pump, leading to embolic consequences including stroke and transient ischemic attack (TIA), and coronary, renal, peripheral or other forms of infarction.

Presently, conventional anti-platelet agents such as aspirin, dipyridamole, pentoxyfylline, theinopyridines, CPTP inhibitors and anti-coagulants, such as heparin, warfarin, rivaroxiban, and direct thrombin inhibitors are used to limit platelet activation and associated biochemical coagulation—involving the intrinsic, extrinsic and common pathways. While these drugs are known to be effective for conventional biochemical stimulation of platelets and coagulation under conditions of low shear, stagnation and pooling, in recent studies it has been demonstrated that these agents have limited or no effect under the "hyper shear" conditions experienced with MCS systems.

As such a need exists to stabilize these cells and protect, insulate and otherwise limit the impact of their high propulsion flow and subsequent sheer on membrane intactness and transmembrane signaling.

Therefore it is an object of the invention to provide compositions, kits, devices, and methods for protecting or insulating cells or to otherwise limit the impact of exogenous physical stimuli on the cells.

It is a further object of the invention to provide improved methods for using devices that apply exogenous physical stimuli on the cells to limit the impact of exogenous physical stimuli on the cells.

SUMMARY OF THE INVENTION

Methods, compositions, and devices to limit, modulate, insulate, and/or otherwise alter the effects of exogenous physical stimuli on cells are described herein. The method includes administering to the cells a composition that limits, modulates, insulates or otherwise alters the effects of exogenous physical stimuli on the cells. The composition is selected from the group consisting of: an effective amount of: (i) one or more agents that modulate cell membrane function and/or stability, (ii) one or more agents that alter submembrane assemblies, (iii) one or more agents that modulate intracellular microfilament function, (iv) one or more agents that intracellular fluid content and tonicity, and combinations thereof, and (v) an external coating to the cells. The one or more agents with the functions disclosed herein and used in the methods described herein are preferably exogenous chemical and biochemical agents. Preferably, the external coating is a polymeric coating. The cells may be removed from the body, preferably isolated, and treated ex vivo with the composition to limit the effects of physical stimuli on the cells and then returned to a patient in need thereof. Alternatively, the cells may be treated in vivo. The compositions can be administered in a variety of manners, such as systemically, locally or regionally. Compositions may be administered orally, parenterally, via catheter, subcutaneously, or by other suitable means. In some embodiments the cells are contacted with a device including the composition(s).

The compositions and methods disclosed herein are useful for patients whose cells experience shear forces, for example, patients needing mechanical circulatory support. An example of such patients include patients with a ventricular assist device.

BRIEF DESCRIPTION OF THE DRAWINGS

FIG. 2A is a bar graph showing the effect of actin modulation on biochemically-induced whole blood activation. Control (left col); cytochalasin b (right col.). FIG. 2B is a line graph showing the effect of actin stabilization/depolymerization drugs on shear-mediated activation of GFP. Control (square), Jasplakinolide (triangle), cytochalasin b (diamond). FIG. 2C is a graph showing DEP stiffness measurements for acting stabilizing/depolymerizing drug-treated platelets. Control (square), Jasplakinolide (triangle), cytochalasin b (diamond).

DETAILED DESCRIPTION OF THE INVENTION

Figure 1A:
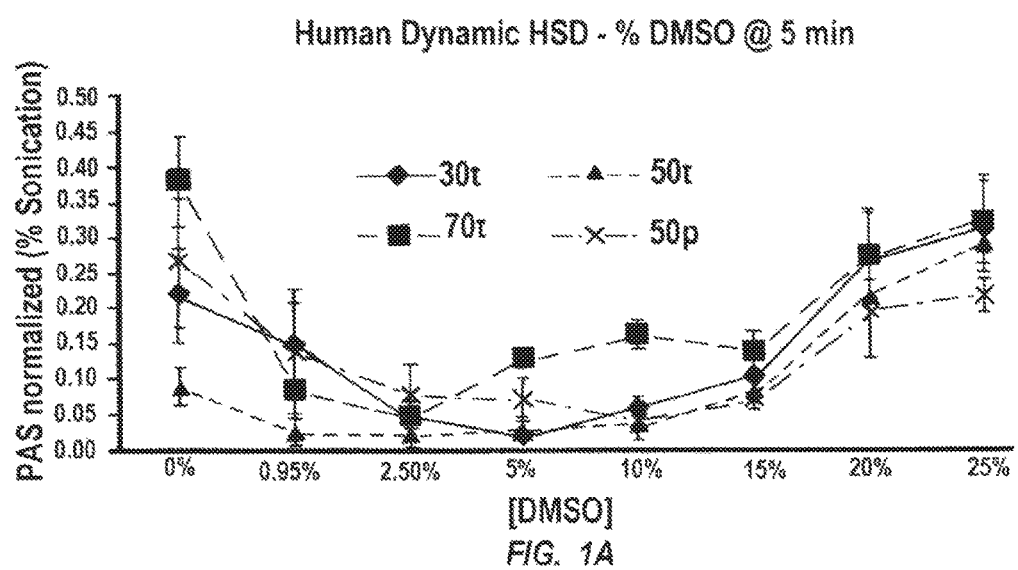
FIG. 1A is a graph of % (v/v/) DMSO versus PAS normalized (% Sonication) for platelets exposed to shear after 5 minutes (diamonds (30τ), triangles (50τ), squares (70τ), and x (50 p)).

Methods, compositions, and devices to limit, modulate, insulate, and/or otherwise alter the effects of exogenous physical stimuli on cells in or from a patient are described herein. Preferably the cells are blood cells, such as white blood cells, red blood cells, and/or platelets, or any circulating somatic cell. The method includes administering to the cells a composition that limits, modulates, insulates or otherwise alters the effects of exogenous physical stimuli on the cells. The composition comprises an effective amount of: (i) one or more agents that modulate cell membrane function and/or stability, (ii) one or more agents that alter submembrane assemblies, (iii) one or more agents that modulate intracellular microfilament function, or (iv) one or more agents that intracellular fluid content and tonicity, and combinations thereof, and (v) an external coating effective to insulate the cells from mechanical stress, and combinations thereof. The one or more agents with the functions disclosed herein and used in the methods described herein are preferably exogenous chemical and biochemical agents.

Preferred agents include lipids and lipid related compounds such as simple fatty acids, glycerolipids, glycerophospholipids, sphingolipids, saccharolipids and polyketides. Sterol lipids and prenol lipids are also useful in the disclosed methods.

The compositions may be administered to the cells passively, i.e. just by contact. Alternatively, active methods for administering the compositions may be used, including but not limited to, ultrasound, electroporation, iontophoresis, applied pressure, etc.

The cells may be removed from the body, preferably isolated, and treated ex vivo to provide a coating, and/or treated ex vivo with a composition that contains one or more agents in an effective amount to alter the effects of exogenous physical stimuli on the cells, and then the treated cells may be administered to the patient.

Alternatively, the cells the compositions disclosed herein are administered in vivo. The disclosed composition or device containing one or more agents in an effective amount to alter the effects of exogenous physical stimuli on the cells may be administered to the patient. The compositions may be administered by a variety of suitable methods, including, but not limited to, orally, systemically, locally, regionally, enterally, parenterally, and subcutaneously. For example, a catheter can be inserted into a patient, and the composition can be infused, perfused, or superfused to the desired site to expose the cells thereto. For regional delivery, the composition may be administered via an osmotic pump.

In some embodiments, the cells can be isolated, treated according to the methods disclosed and claimed herein, stored and reinfused into an animal, including man.

In some embodiments the cells are contacted with a device including the composition(s). For example, the composition can be included in a stent, or paving layer, or other blood contacting device. For example, one or more materials that alter the effects of exogenous physical stimuli on the cells may be admixed into a polymer depot that is applied to cells. Suitable techniques are known and include, but are not limited to solid paving and coating. In some embodiments, the composition(s) is coated on all or part of the cells.

Following administration, the membrane function and stability, most specifically fluidity, of the cells may be modulated. Alternatively or additionally, the sub-membrane assemblies involved in mechano-transduction may be modulated following administration of the compositions and devices. Alternatively or additionally, the intracellular microfilament function may be modulated following administration of the compositions and devices. Alternatively or additionally, the intracellular microtubule function may be modulated following administration of the compositions and devices. Alternatively or additionally, the intracellular fluid content and tonicity may be modulated following administration of the compositions and devices.

The compositions and methods disclosed herein are useful for patients whose cells experience shear forces, for example, patients needing mechanical circulatory support such as a ventricular assist device. There are now a variety of circulatory assist devices, including VADs for the left ventricle (LVADs), right ventricle (RVADs), or both chambers (biventricular VADS, or BVADs) as well as full artificial hearts. In some embodiments, despite the fact that mechanical activation is prevented, biochemical activation still occurs. Thus, the agent selected can reduce responsiveness to mechanical activation while maintaining biochemical activation.

I. Definitions

"Modulate cell membrane function and/or stability" as used herein means to alter its function with respect to it fluidity (lateral diffusion of contained components, i.e. transmembrane proteins—e.g. integrins, gplb, etc); its stiffness—impacting overall cell stiffness; it porogenicity—i.e. permeability to various agents; specific pores, transporters or pumps—e.g. shear-dependent channels; and/or its cholesterol and other lipid and intercalating compound content.

"Alter submembrane assemblies" as used means to alter the levels and/or function of submembrane assemblies.

"Modulate intracellular microfilament function" as used herein means to increase polymerization/organization of actin and other intracellular microfilaments or decrease synthesis, depolymerize or block function "Modulate intracellular microtubule function" as used herein means can either increasing their polymerization and assembly, leading to a net increase in cell stiffness or depolymerizing microtubules leading to a decrease in stiffness "Modulate intracellular fluid content and tonicity" as used herein means changing the internal ionic milieu which contributes to cell tonicity—which effects overall cell shape and stiffness, e.g. hoptonicity makes cell have increasing intracellular pressure due to swelling, changing stiffness.

"Submembrane assemblies" as used herein are the collection of physical linker proteins, enzymes, kinases and other molecular transducers that convert mechanical signal/energy into biochemical signals and reactions, able to effect intra and inter-cellular processes, e.g. transcription or protein activation via phosphorylation.

II. Modulation of Membrane Function and Stability

The disclosed method includes administering to cells, a composition that includes one or more agents in an effective amount to modulate of membrane function and stability, in particular fluidity. Alteration of membrane fluidity via exogenous agents is effective to "rubberize" the membrane, thereby allowing it to tolerate more exogenous physical force and shear, effectively desensitizing it to these stimuli.

In some preferred embodiments, the one or more agents are effective to increase membrane fluidity and/or reduce membrane stiffness. In other preferred embodiments, the one or more agents are effective to decrease membrane fluidity and/or increase membrane stiffness. By way of example data is presented in the Examples section.

Preferred agents are lipids and lipid related compounds. Lipids may be broadly defined as hydrophobic or amphiphilic small molecules; the amphiphilic nature of some lipids allows them to form structures such as vesicles, multilamellar/unilamellar liposomes, or membranes in an aqueous environment. Useful lipids include fatty acids, glycerolipids, glycerophospholipids, sphingolipids, saccharolipids, and polyketides (derived from condensation of ketoacyl subunits); and sterol lipids and prenol lipids (derived from condensation of isoprene subunits).

Agents that are capable of modulating membrane fluidity include but are not limited to, dimethysulfoxide (DMSO), gangliosides, interpolating lipids, hormones, or sterols, cholestrol, cholesterol hemisuccinate, lidocaine, procaine, sex steroids, phenytoin, Docohexanoic acid, cortisol, estradiol, PGE2, progesterone, medroxyprogesterone, insulin, glucagon, atropine, carbachol, lutropin, neuropeptide Y, thyroid hormone, aldosterone, vasopressin, perylene, 9-(dicyanovinyl) julodinine, 1,6-diphenyl-1,3,5-hexatiene (DPH), TMA-DPH, DPH-PA, cis and trans-parinaric acid, polyunsaturated fatty acids, phospatidyl choline, phospahtidylserine, phosphatidyl inositol, insitol, choline, cerebroside, glycoshpingolipids, and sphingomyelin. For example, one or more of these agents may be included in the materials or devices and administered to cells, preferably blood cells, such as platelets, to limit shear-mediated platelet aggregation. In preferred embodiments, the materials and devices include dimethysulfoxide (DMSO), gangliosides, interpolating lipids, hormones, or sterols, or combinations thereof. These agents can be administered alone, or in combination with other agents disclosed herein such as the polymeric coating, agents that alter submembrane assemblies, modulate intracellular microfilament or microtubule function or agents that modulate intracellular fluid content and tonicity. In a preferred embodiment, the cholesterol administered is non-atherogenic.

DMSO is an organosulfur compound utilized as solvent and skin penetrant. DMSO is commonly used as an organic solvent for inactive antiplatelet drugs where they have to be metabolized to produce active metabolite. DMSO has been employed in cell biology to induce cell fusion, differentiation and cryo-preservation.

As noted above, cell surface integrins, such as platelet integrins, serve as biochemical receptors or antenna to capture exogenous physical force stimuli. In the case of blood flow integrins serve as shear-sensitive receptors. As shear increases, due to repetitive exposure, or turbulence, or increasing hyper shear levels, integrins may be stimulated leading to signal transduction and platelet activation. This activation involves shape change, release of numerous platelet granules and biochemical mediators and exposure of membranes elements, leading to activation of the biochemical cascades of coagulation resulting in thrombin generation and conversion of fibrinogen to fibrin, resulting in an active clot.

The compositions disclosed herein may be administered to one or more cells, to alter cell membrane function, to make it more resilient to the impact of shear forces. An example of this approach is to alter membrane fluidity. For example, in the case of platelets, the composition can be used to alter platelet membrane function, preferably fluidity. Alteration of platelet membrane fluidity results in the platelet having greater resilience to damage from physical forces. This leads to a preservation of normal integrin signaling, i.e. via prevention of accidental or sub-threshold signaling via "wobble" or physical instability of integrins in the membrane, or leakiness of the membrane, leading to concomitant biochemical activation. Further, alteration of membrane fluidity will induce inadvertent pore formation and membrane fragmentation due to shear.

III. Alteration of Sub-Membrane Assemblies Involved in Mechano-Transduction

The disclosed method includes administering to cells a composition containing one or more agents in an effective amount to alter sub-membrane assemblies involved in mechano-transduction. Examples of proteins and molecular transducers involved in mechano-tranduction have been described for example in Zaidel-Bar, et al., 32:416-420 (2004); Bershadsky, et al., *Current Opinion in Cell Biology*, 18:472-481 (2006), Wehrle-Haller, et al., *Trends in Cell Biology*, 12(8):382-389 (2002); Geiger, et al., *Cell*, 110:139-142 (2002); and Geiger, et al. *Current Opinion in Cell Biology*, 13:584-592 (2001). In some preferred embodiments, the one or more agents are effective to increase the level and/or activity of sub-membrane assemblies. In other preferred embodiments, the one or more agents are effective to decrease the level and/or activity of sub-membrane assemblies.

The cells are preferably blood cells. These agents can be administered alone, or in combination with other agents disclosed herein such as the polymeric coating, agents that alter membrane fluidity, modulate intracellular microfilament or microtubule function or agents that modulate intracellular fluid content and tonicity.

Suitable agents include, but are not limited to NSAIDs, e.g. sulindac sulfide, and phenolic antioxidants, caffeic acid phenethyl ester (CAPE), which may modulate Focal Adhesion Kinase (FAK, also known as PTK2 protein tyrosine kinase 2 (PTK2)) signaling. Weyant, et al., "Colon cancer chemoprotective drugs modulate integrin-mediated signaling pathways", *Clin Cancer Res,* 6:949 (2000). Similarly resveratrol may modulate FAK as well.

Rho kinase inhibitors, e.g. Y-27632 including FAK, talin and other linkage and phosphorylated proteins, may be included in the compositions in an effective amount to limit shear-mediated platelet activation, and administered to the cells.

Additional useful agents include, but are not limited to, phenolic antioxidants, caffeic acid phenethyl ester (CAPE) FAK signaling and modulating agents, resveratrol, Rho kinase inhibitors, e.g. Y-27632, inhibitors or modulators of talin, paxilin, and viculin and similar submembrane mcchnotrasnductive proteins.

IV. Modulation of Intracellular Microfilament Function

The compositions used in the methods disclosed herein may contain one or more agents in an effective amount to modulate intracellular microfilament function. In some preferred embodiments, the one or more agents are effective to increase the microfilament assembly and/or integrity. In other preferred embodiments, the one or more agents are effective to decrease to increase the microfilament assembly and/or integrity.

Suitable agents that are capable of modulating intracellular microfilament function include, but are not limited to, cytochiasins (e.g. cytochlasin B), concanavalin, vincristine, vinblastine, oryzalin, trifluralin, taxol, taxetere and similar compounds.

These agents can be administered alone, or in combination with other agents disclosed herein such as the polymeric coating, agents that alter membrane fluidity, or submembrane assemblies, agents that modulate intracellular microtubule function or intracellular fluid content and tonicity.

V. Modulation of Intracellular Microtubule Function

The compositions used in the methods disclosed herein may contain one or more agents in an effective amount to modulate intracellular microtubule function. In some preferred embodiments, the one or more agents are effective to increase the microtubule assembly and/or integrity. In other preferred embodiments, the one or more agents are effective to decrease to increase the microtubule assembly and/or integrity.

Suitable agents that are capable of modulating intracellular microtubule function include, but are not limited to colchicine, colcemid, vinblastine, vincristine, taxol, taxetere, 9-bromonscapine (EM011), docetaxel, noscapinoids, and tau.

These agents can be administered alone, or in combination with other agents disclosed herein such as the polymeric coating, agents that alter membrane fluidity or submembrane assemblies, or agents that modulate intracellular microfilament, or intracellular fluid content and tonicity.

VI. Modulation of Intracellular Fluid Content and Tonicity

The compositions used in the methods disclosed herein may contain one or more agents in an effective amount to modulate intracellular fluid content and tonicity. For example, the compositions may include hypo or hypertonic solutions, for example, saline, lactated ringers, dextrose, sucrose, mannitol, or similar small molecules.

In these embodiments, the cells may be contacted (in vivo) with or incubated ex vivo in hypo or hypertonic solution. The cells may also be contacted with aqueporin receptors modulating agents, agonists or antagonists, Hg $Cl_2$, G-protein modulating agents, vasopression receptors modualtors, including V1a, V1b and V2, tolvaptan, convivaptan, and/or other vaptans.

Aqueporin receptors may be modulated via Hg $Cl_2$. See Lee, et al., "Water channels in platelet volume regulation", *J Cell Mol Med,* 16:945 (2012)). G-proteins may be modulated. And vasopression receptors, notably V1a and V1b, may be modulated by these treatments.

These agents can be administered alone, or in combination with other agents disclosed herein such as the polymeric coating, agents that alter membrane fluidity or submembrane assemblies, or agents that modulate intracellular microfilament All of the above methodologies and therapeutics alter the tonicity, and/or enhance the tension or state of expansion of a cell. By virtue of alteration of stiffness and compliance of the cell, the sensitivity of cellular reactivity to exogenous physical forces is also altered.

VII. Providing an External Coat or Coating to Cells

The disclosed methods include coating the cells are coated with a surface coating or interdigitated coating. The cell coating contemplated in this embodiment is a coating that serves the functions as a mechanical buffer.

The cell coating may be a full or partial coating, made either in isolation, ex vivo or in situ to limit exogenous stimulation via physical forces, preferably shear forces. Preferably, the coating is a polymeric coating.

Cells may be removed from the body, purified and subjected to coatings, interdigitating (in the membrane) coating materials ex vivo and then be stored and re-injected as needed. Preferably the cells are blood cells, such as platelets, red blood cells (RBC) or white blood cells (WBC).

The blood cells are removed from a subject and exogenously treated to affix an exogenous coat or an interdigitating coat, i.e. complete enclosure of a single or group of cells. This approach may be applied to other tissue cells that may be isolated or partitioned as single cells or as cell clusters or tissue fragments.

Suitable media for coating cells in part or in whole includes natural and synthetic materials, including but not limited to natural and synthetic polymers. Suitable natural materials for use in this embodiment include, but are not limited to alginate, a natural product from brown algae (seaweed), carrageenan, xanthan gums, chitosan, agarose, agar, collagen, cellulose and its derivatives, hyaluronate, pectin, fibrin, protein, nucleic acids and gelatin. Suitable synthetic materials that can be used in the disclosed method include, but are not limited to, epoxy resin, photo crosslinkable resins, poly(vinyl alcohol), PEG-lactide hydrogels, PEG-glycolide hydrogels, PEG-lactide-co-glycolide hydrogels Eudragit, Pluronics and Tetronics, polyacrylamide, polyester, polystyrene, poly(acrylic acid), poly(ethylene oxide), poly-L-ornithine and poly(methylene-co-guanidine) hydrochloride, polyphosphazene, and polyurethane.

In some applications, two or more materials may be used as the coating medium, for example, alginate and polyvinyl alcohol or copolymers of poly(ethylene oxide) and poly (propylene oxide) or of poly(ethylene oxide) and poly(lactic acid) could be used as a coating matrix.

A variant of complete encapsulation is to selectively coat regions of the cell membrane or coat, shield or otherwise locally provide and an "umbrella" or "shield" for selective membrane receptors, such as integrins.

Interdigitating polymers may include adducts involving a lipid or hydrophobic tail grafted to a PEG, PEG-lactide, or all or any synthetic and natural polymeric materials listed above. See Du, et al., "Grafted poly-(ethylene glycol) on lipid surfaces inhibits protein adsorption and cell adhesion", *BBA Biomembranes,* 1326:236 (1997); and Marsh, et aL, "Lipid membranes with grafted polymers: physicochemical aspects", *BBA Biomembranes,* 1615:33, (2003).

EXAMPLE

Example 1

Effect of DMSO on the Activation and Aggregation of Biochemically, or Shear-Induced Platelets Human blood was collected from healthy volunteers in citrated buffers. Platelet rich plasma (PRP) and gel-filtered platelets (GFP) were isolated as previously described (Girdhar, et al., *PLOS One,* 7(3):e32463 (2012)) then treated with percentages of DMSO (v/v) ranging from 0.95%-60%. Platelet activity state (PAS) assay of GFP sheared at 30 dyne/cm$^2$ via con-plate viscometer and light transmission aggregometry (LTA) of PRP and GFP induced by ADP and collagen were performed. 5% DMSO (v/v) was observed to be the most effective in protecting platelets from activation induced by constant shear stress and aggregation induced by chemical agonists. PAS assay showed that at 5 min of 30 dyne/cm$^2$, 5% DMSO can protect the platelet up to 90% in comparison to control. In contrary, when platelets were exposed to a longer time of 10 min, the same level of protection shifted to 10% DMSO; suggesting that there is a correlation in the intensity of shear stress and the level of protection. PAS results were further confirmed by the LTA, where the 5% of DMSO-pretreated platelets had lower maximal aggregation and slower platelet aggregation rate. These findings suggest that DMSO can deactivate platelets.

Light transmission aggregometry (LTA) was performed to detect platelet desensitization using arachidonic acid, ADP, collagen, epinephrine, and ristocetin. Platelets were fixed and visualized at the varying DMSO treatments under scanning electron microscopy (SEM). Collagen and epinephrine had limited effect on PRP aggregation ranging from 0.95% to 10% of DMSO. Samples showed an inhibition at 10% and 5% DMSO when treated with ADP and arachidonic acid, respectively. DMSO has no effect on ristocetin-induced platelet aggregation. SEM of platelets at 5% and 10% showed significant reduction in filopodia (data not shown).

DMSO altered platelets membrane fluidity and desensitized their aggregability from certain common agonists; thus reflecting the role of DMSO in some biochemical pathways that inhibit platelets.

In some experiments, varying percentages of DMSO were added to platelets, which were then subjected to defined sheer. As shown in the FIG. 1A, a protective effect, despite exposure to shear (30-70 dynes/cm$^2$) was observed for DMSO over the concentration range of 0.5 to 25%, with the best effect seen at about 1-5%. This study demonstrates that alteration of membrane fluidity utilizing an exogenous agent is able to reduce the sensitivity of platelets to shear-mediated activation.

Figure 1B:
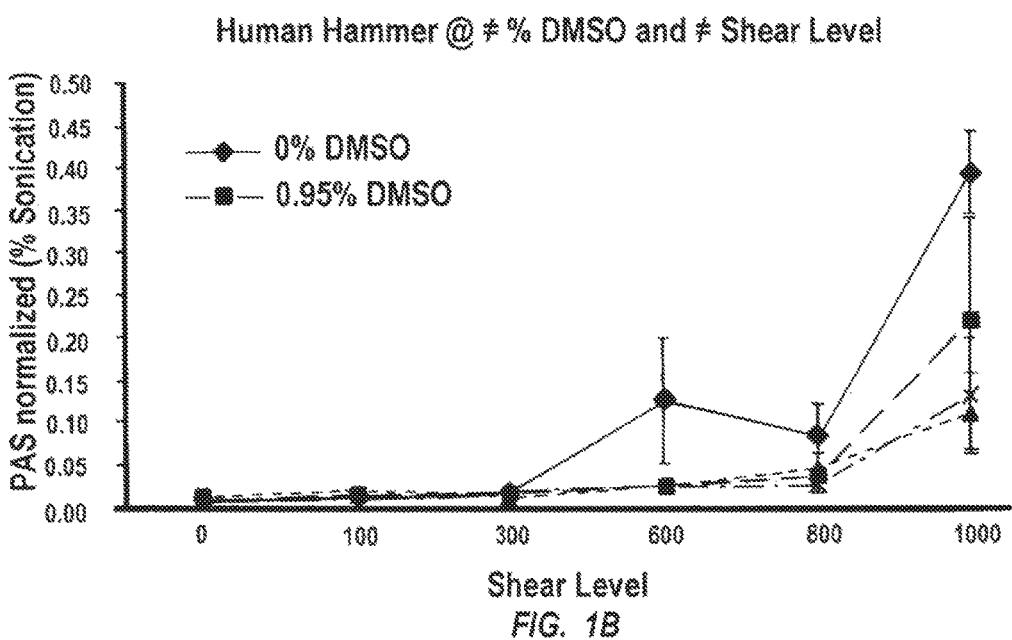
FIG. 1B is a graph of shear level (ranging from 0 to 1,000 dynes/cm$^2$) versus PAS normalized (% Sonication) for platelets exposed to 0% DMSO (diamonds) and 0.95% (v/v) DMSO at varying levels of shear.

To further extend the above observation, platelets were pre-incubated with DMSO, at 0.95% (v/v), and then subjected to much higher levels of shear via a platelet hammer device, i.e. shear from 100-1000 dynes/cm$^2$. As shows in FIG. 1B, it was observed that with optimal DMSO pre-incubation, platelets were able to tolerate much higher levels of sheer, i.e. hyper shear, at levels an order of magnitude greater than in the above study. These levels correlate with the levels experienced in VADs and other high shear MCS devices.

Figure 1C:
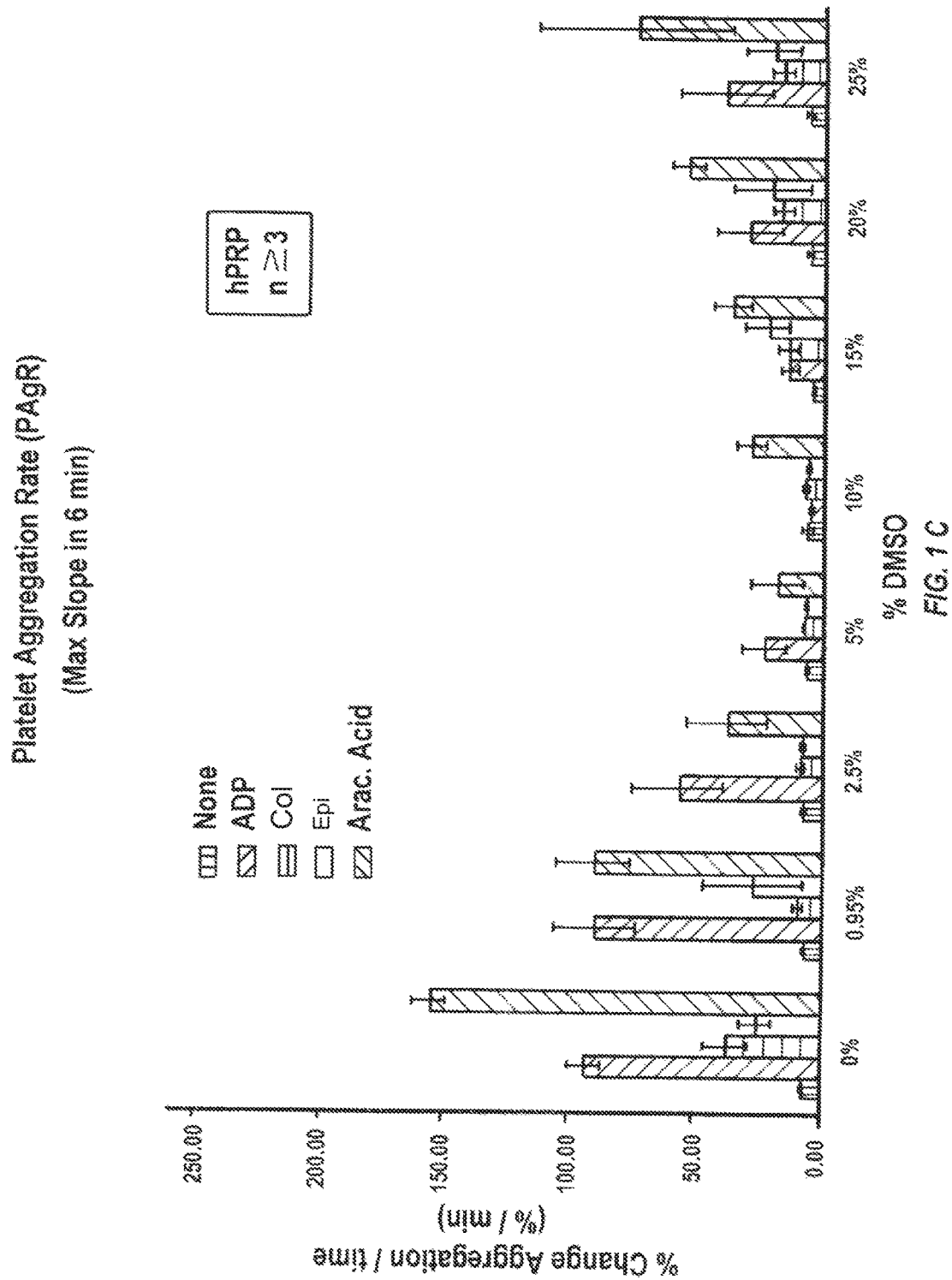
FIG. 1C is a bar graph of Platelet Aggregation Rate showing platelets subjected to different percent DMSO formulations (0% to 25% (v/v) and different agents (none (1$^{st}$ bar), ADP (2$^{nd}$ bar), CO (3$^{rd}$ bar), Epi (4$^{th}$ bar), and Arac. Acid (5$^{th}$ bar)) versus percent change in aggregation/time (%/min), for hPRP n≥3.

To examine whether membrane modulation impacted biochemical as well as shear-mediated platelet activation the following study was performed. Platelet rich plasma (PRP) was pre-incubated with varying concentrations of DMSO. PRP was then exposed to a variety of chemical agonists (ADP, Col, EpPi, Arac. Acid, or none (control)). A similar reduction of agonist-mediated activation was noted as with the shear-exposure experiments above, though for chemical activation, the inhibitory peak for DMSO appeared to be shifted to the right, i.e. at higher DMSO concentrations. See FIG. 1C.

Example 2

Effect of Microfilament Modulation on Biochemical or Shear-Induced Platelet Activation Platelets were collected from human volunteers and PRP obtained as described above. Platelet-activation was determined (biochemical vs. shear mediated) was determined within the context of modulation of intracellular microfilament action, as measured by the effect on actin was determined. Actin is a globular multi-functional protein that forms microfilaments. It is found in almost all eukaryotic cells where it may be present at concentrations of over 100 μM. An actin protein's mass is roughly 42-kDa and it is the monomeric subunit of two types of filaments in cells: microfilaments, one of the three major components of the cytoskeleton, and thin filaments, part of the contractile apparatus in muscle cells. It can be present as either a free monomer called G-actin (globular) or as part of a linear polymer microfilament called F-actin (filamentous).

Whole blood aggregation was determined in the presence of ADP in cells treated with cytochalasin B (FIG. 2A). Cystochalasin B inhibits both the rate of actin polymerization and the interaction of actin filaments in solution. Maclean-Fletcher, *Cell,* 20(2):329-41 (1980). The effect of actin stabilizing/depolymerization drugs (Jasplakinolide and cystochalasin B) in shear-mediated platelet activation was measured in GFP. Jasplakinolide, a cyclo-depsipeptide, is an actin filament polymerizing and stabilizing drug (reviewed in Visegrady, et al., *FEBS Lett,* 565 (1-3):163-166 (2004)). The data (FIG. 2B) shows that compared to control cells (with 0.1% DMSO), GFP experience less activation over time in the presence of the actin stabilizer in response to a 70 dyn shearing force. Platelet stiffness was characterized by electrodeformation using Dielectrophoresis (DEP). DEP is the lateral motion generated on uncharged particles due to polarization induced by non-uniform electric fields. DEP stiffness measurements for actin stabilizing/depolymerization drug treated platelets are shown in in FIG. 2C.

Example 3

Effect of Microtubule Modulation on Shear-Induced Platelet Activation

Figure 3A:
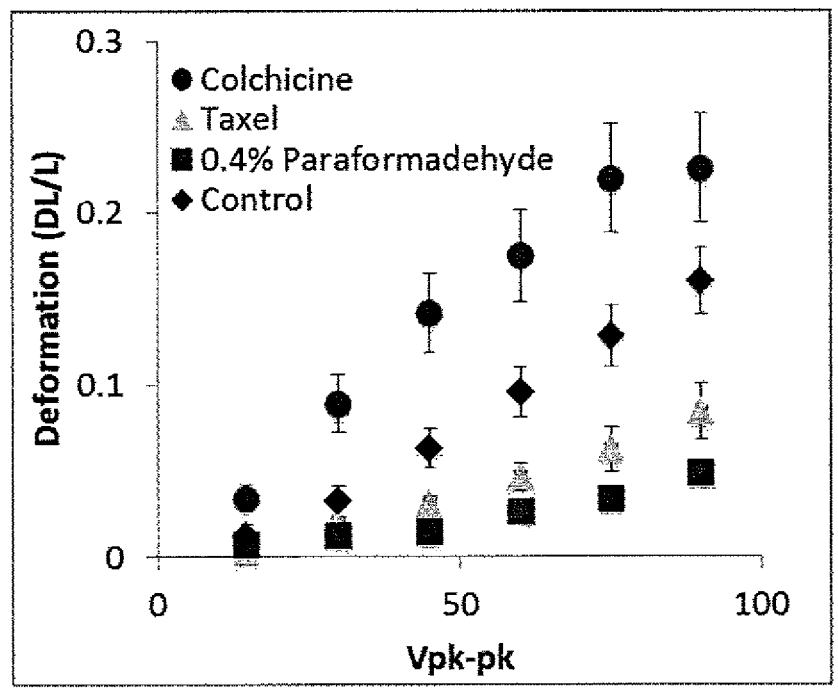
FIG. 3A is a line graph showing the effect of microtubule modulating drugs on platelet stiffness. Cholchicine (circle), Taxel (triangle), 0.4% paraformaldehyde (square) and control (diamond).
Figure 3B:
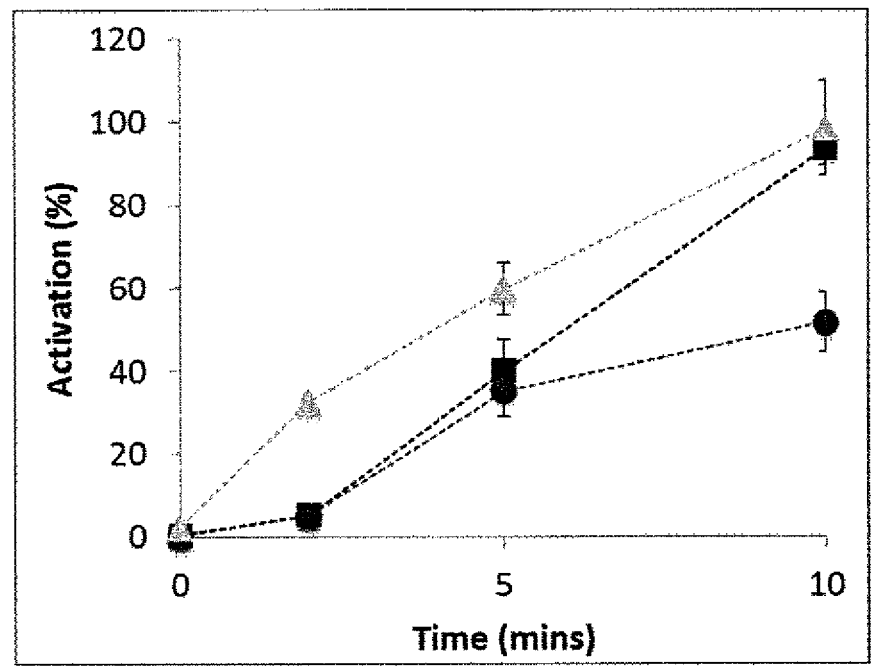
FIG. 3B is a graph showing time dependent platelet activation induced by a 70 dyn shear force in the presence of microtubule modulating agents. circle=colchicine; trangle=taxel; and square=control.

Platelets were obtained as previously described and the effect of microtubule modulation on biochemical or shear-induced (70 dyn shearing force) platelet activation was determined. Microtubule modulation was effected using colcichine and taxol, for example. Cochicine has been shown to inhibit mictotuble polymerization. Skoufias, *Biocehmistry,* 31(3):738-746 (1992). Taxol on the other has been shown to stabilize microtubules. Arnal, et al., *Curr. Biol.,* 5(8):900-908 (1995). The effect of these agents on platelet stiffness when compared to control is show in in FIG. 3A. Shear-induced platelet activation in the presence of these microtubule modulators was also determined and is shown in FIG. 3B.

Example 4

Effect of Membrane Modulation on Biochemical and Shear-Induced Platelet Activation Platelets were obtained as previously described and the effect of microtubule modulation on biochemical or shear-induced (70 dyn shearing force) platelet activation was determined. Membrane modulation was effected using hydrophobic molecules such as Docosahexaenoic acid (DHA) and Eicosapentaenoic acid (EPA), the structures of which are shown below.

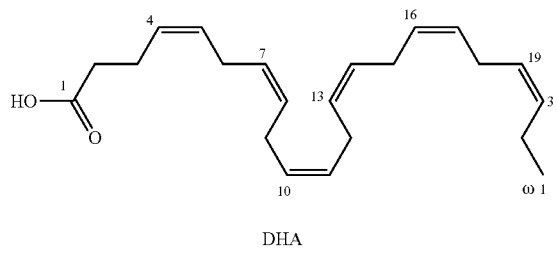 [SMILES: CC/C=C\C/C=C\C/C=C\C/C=C\C/C=C\C/C=C\CCC(=O)O ; "DHA"]

DHA

DHA at pH 7, decreases the bilayer stiffness, consistent with an amphiphile-induced increase in elasticity.

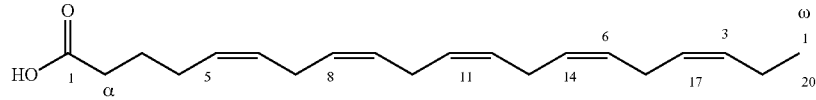 [SMILES: CC/C=C\C/C=C\C/C=C\C/C=C\C/C=C\CCCC(=O)O]

EPA increases hydrophobicity in 1K-1 cells.

Figure 4A:
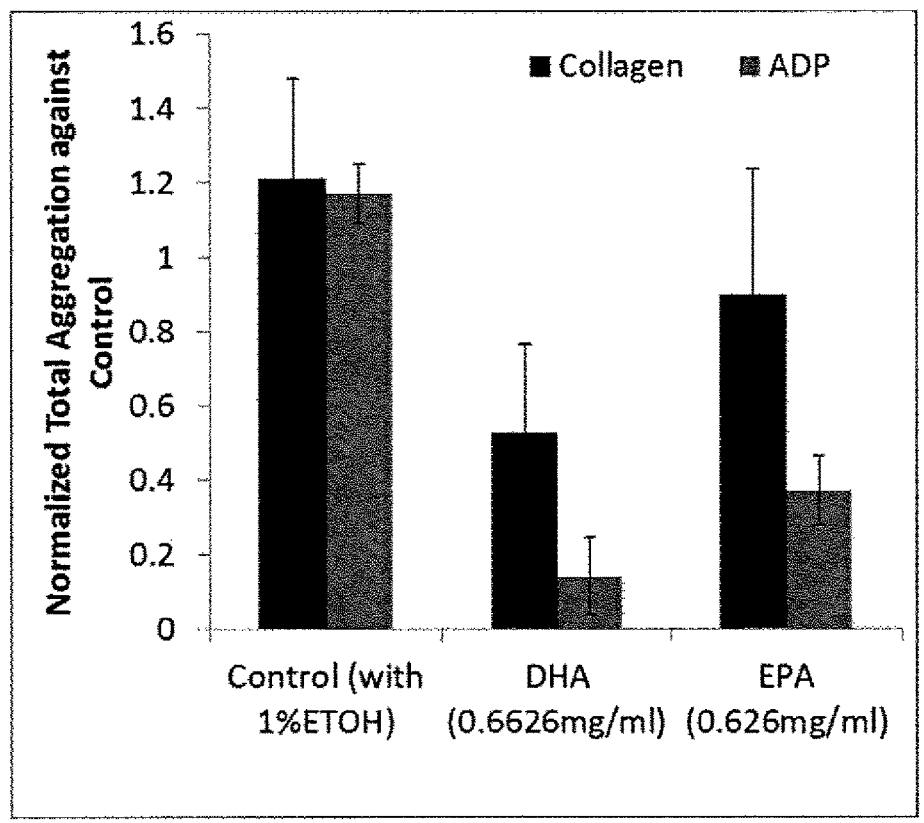
FIG. 4A is a bar graph showing the effect of DHA and EPA on collagen and ADP-induced platelet (PRP) activation.

The effect of DHA and EPA on biochemically induced platelet activation using PRP is shown in FIG. 4A. Platelet activation was induced by treating cells with ADP or collagen as previously described. The effect of DHA and EPA on ADP or collagen induced platelet activation (as measured by platele aggregation, was compared to control cells (with 1% ETOH). DHA and EPA each reduced platelet aggregation observed with collagen and ADP treatment.

Figure 4B:
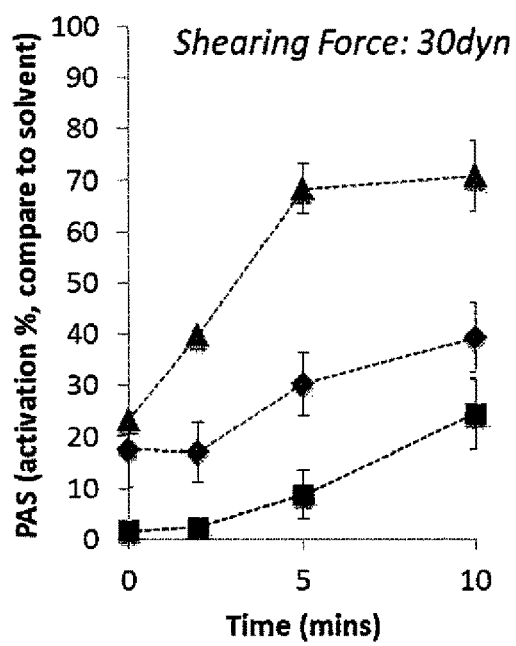
FIG. 4B is a graph showing the effect of DHA (0.626 mg/ml; triangle) and EPA (0.626 mg/ml; diamond), compared to control (square) on shear-induced (30 dyn) platelet activation.
Figure 4C:
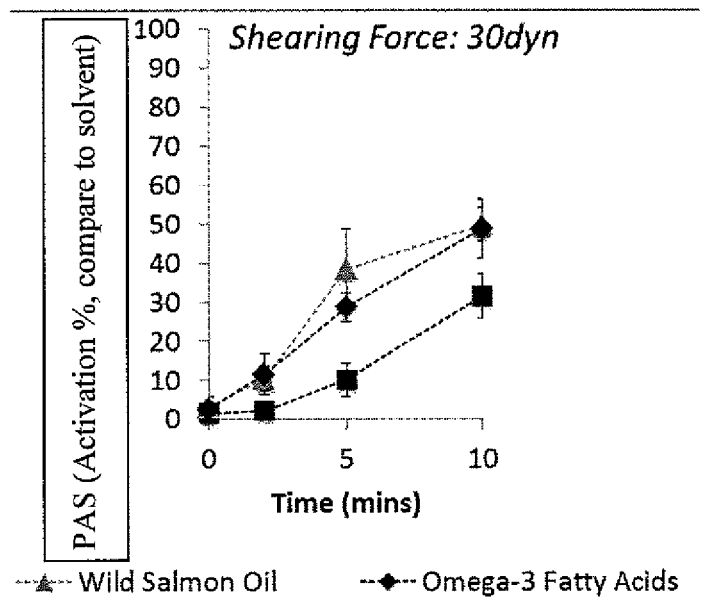
FIG. 4C is a graph showing the effect of wild salmon oil (triangle) and omega-3 fatty acids (diamond), compared to control (square), on shear-induced (30 dyn) platelet activation.

Shear-mediated platelet activation was also measured in the presence of DHA, EPA and wild salmon oil (FIG. 4B-C).

Figure 4D:
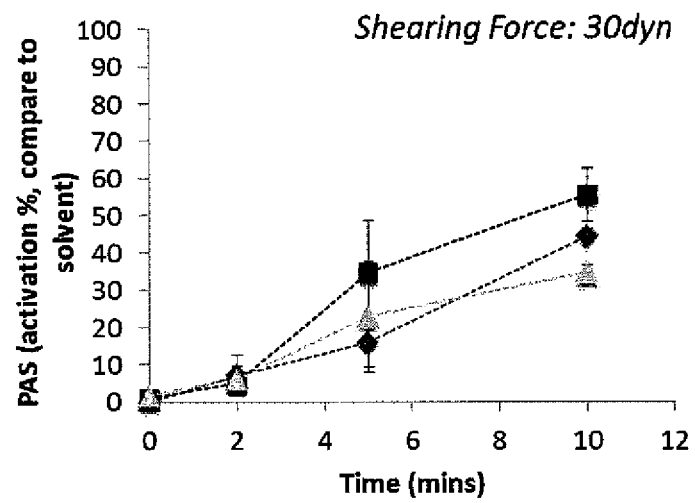
FIG. 4 Dis a graph showing the effect of 20 μM cholesterol (diamond) and 200 μM cholesterol (triangle) compared to 0.1% DMSOs (square), on shear-induced (30 dyn) platelet activation.
FIG. 4E is a graph showing the effect of 20 μM cholesterol (diamond) and 200 μM cholesterol (triangle) compared to 0.1% DMSOs (control; square), on shear-induced (70 dyn) platelet activation. All plots n>3, Error: Std error.
FIG. 4F is a bar graph showing the effect of lecithin (100 μg/ml) on ADP-induced platelet (PRP) activation.
FIG. 4G is a graph showing the effect of lecithin on shear-induced (30 dyn) platelet (GFP) activation. Control (diamond); lecithin (25 ug/ml; square).
Figure 4E:
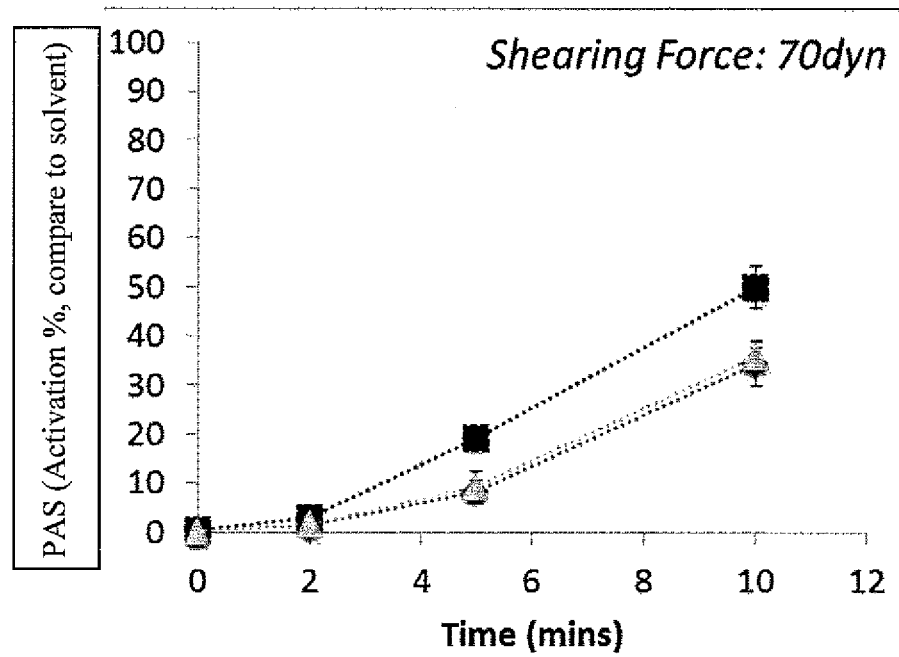
Figure 4F:
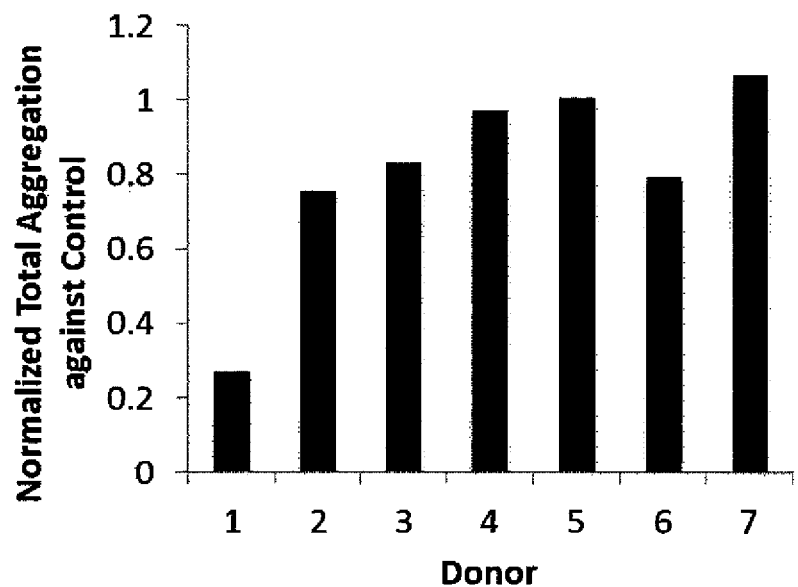
Figure 4G:
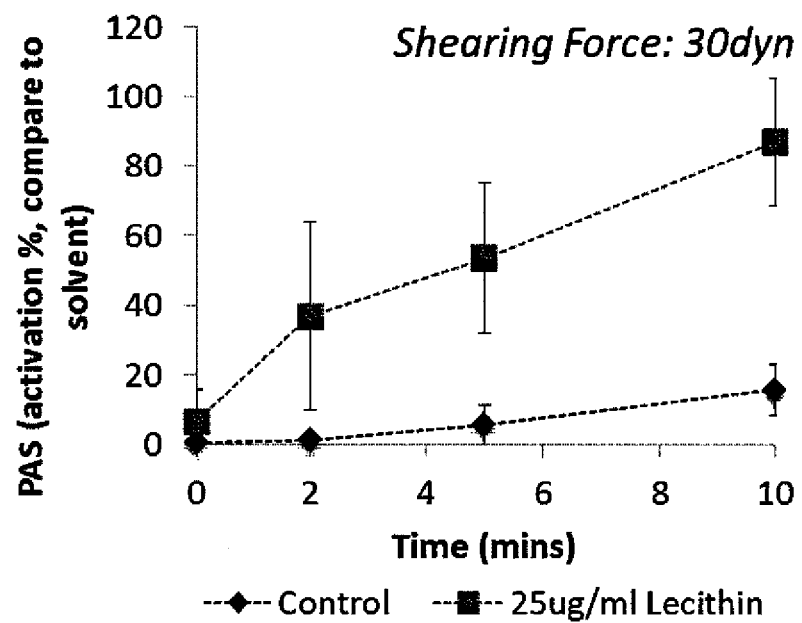

Shear-mediated and biochemical mediated platelet activation was also measured in the presence of the amphipathic molecules, cholesterol and lecithin. Cholesterol adds firmness and integrity to the plasma membrane and prevents it from becoming overly fluid i.e., cholesterol helps the membrane maintain its fluidity. In the studies including cholesterol, cholesterol-treated cells were compared with cells treated with 0.1% DMSO. The data shown in FIG. 4D-E, shows that cholesterol reduces shear-induced platelet activation at both concentrations used. The data for lecithin is shown in FIGS. 4F and G. As shown in FIG. 4G, shear-induced platelet activation as measured by PAS increases in the presence of lecithin, when compared to controls. The data in this example shows that DHA, EPA and lecithin increase platelet sensitivity to shear stress.

I claim:
1. An ex vivo or in vivo method of treating human cells to modulate their reactivity to exogenous physical forces comprising administering to human cells subjected to exogenous physical forces, a composition comprising an effective amount of one or more agents selected from the group consisting of:
(i) a lipid or lipid related compound, hormone, carbachol, atropine, inositol, DMSO, lidocaine, procaine, sex steroids, phenytoin, perylene, 9-(dicyanovinyl) julodinine, 1,6-diphenyl-1,3,5-hexatiene (DPH), TMA-DPH, DPH-PA, cis and trans-parinaric acid, wherein the hormone is selected from the group consisting of cortisol, estradiol, progesterone, medroxyprogesterone, insulin, glucagon, thyroid hormone, and aldosterone;
(ii) sulindac sulfide, phenolic antioxidants, caffeic acid phenethyl ester (CAPE) FAK signaling and modulating agents, resveratrol, Rho kinase inhibitors, Y-27632, inhibitors or modulators of talin, paxilin, and viculin and submembrane mechnotransductive proteins;
(iii) cytochlasins, concanavalin, vincristine, vinblastine, oryzalin, trifluralin, taxol, and taxetere;
(iv) colchicine, colcemid, 9 bromonscapine (EM011), docetaxel, noscapinoids, and tau; or
(v) hypo or hypertonic solutions, saline, lactated ringers, dextrose, sucrose, and mannitol, aqueporin receptors modulating agents, Hg Cl2, G-protein modulating agents, tolvaptan, convivaptan, and vaptans
wherein the exogenous physical force provides a shear stress greater than 50 dynes/cm$^2$, wherein the method further comprising using a ventricular assist device (VAD) to pump blood in a patient's body, wherein the exogenous physical force is a force provided by the VAD.

2. The method of claim 1, wherein the lipid or lipid related compound is selected from the group consisting of fatty acids, glycerolipids, glycerophospholipids, sphingolipids, saccharolipids, polyketides, sterol lipid, and prenol lipid.

3. The method of claim 1, wherein the cells comprise one or more of platelets, red blood cells, white blood cells, and circulating precursor and stem cells, and wherein the composition is applied to the cells.

4. The method of claim 1, wherein the shear force provides a shear stress of greater than or equal to about 1,000 dynes/cm$^2$.

5. The method of claim 1, wherein the agent is selected from the group consisting of Ganglio sides, cholesterol, cholesterol hemisuccinate, lidocaine, procaine, sex steroids, phenytoin, Docohexanoic acid, PGE2, neuropeptide Y, polyunsaturated fatty acids, phosphatidyl choline, phosphatidylserine, phosphatidyl inositol, inositol, choline, cerebroside, glycosphingolipids, and sphingomyelin.

6. The method of claim 1, the force provides shear stress between a shear force of about 200 dynes/cm² to a shear force of about 1000 dynes/cm².

7. The method of claim 6, wherein the force provides shear stress of 500 dynes/cm² or greater.

8. An ex vivo or in vivo method of treating cells to modulate their reactivity to exogenous physical forces comprising administering to cells subjected to exogenous physical forces, a composition comprising an effective amount of one or more agents selected from the group consisting of:
 (i) carbachol, atropine, inositol, DMSO, lidocaine, procaine, sex steroids, phenytoin, perylene, 9-(dicyanovinyl) julodinine, 1,6-diphenyl-1,3,5-hexatiene (DPH), TMA-DPH, DPH-PA, cis and trans-parinaric acid;
 (ii) sulindac sulfide, phenolic antioxidants, caffeic acid phenethyl ester (CAPE) FAK signaling and modulating agents, resveratrol, Rho kinase inhibitors, Y-27632, inhibitors or modulators of talin, paxilin, and viculin and submembrane mechnotransductive proteins;
 (iii) cytochlasins, concanavalin, vincristine, vinblastine, oryzalin, trifluralin, taxol, and taxetere;
 (iv) colchicine, colcemid, 9 bromonscapine (EM011), docetaxel, noscapinoids, and tau; and
 (v) hypo or hypertonic solutions, saline, lactated ringers, dextrose, sucrose, and mannitol, aqueporin receptors modulating agents, agonists or antagonists, Hg Cl2, G-protein modulating agents, vasopressin receptors modulators, tolvaptan, convivaptan, and vaptans
 wherein the exogenous physical force provides a shear stress of about 200 dynes/cm² or greater.

9. An ex vivo or in vivo method of treating human cells to modulate their reactivity to exogenous physical forces comprising administering to human cells subjected to exogenous physical forces, a composition comprising an effective amount of one or more agents selected from the group consisting of:
 (i) a lipid or lipid related compound, carbachol, atropine, inositol, DMSO, lidocaine, procaine, sex steroids, phenytoin, perylene, 9-(dicyanovinyl) julodinine, 1,6-diphenyl-1,3,5-hexatiene (DPH), TMA-DPH, DPH-PA, cis and trans-parinaric acid;
 (ii) sulindac sulfide, phenolic antioxidants, caffeic acid phenethyl ester (CAPE) FAK signaling and modulating agents, resveratrol, Rho kinase inhibitors, Y-27632, inhibitors or modulators of talin, paxilin, viculin and submembrane mechnotransductive proteins;
 (iii) cytochlasins, concanavalin, vincristine, vinblastine, oryzalin, trifluralin, taxol, and taxetere;
 (iv) colchicine, colcemid, 9-bromonscapine (EM011), docetaxel, noscapinoids, and tau;
 (v) hypo or hypertonic solutions, saline, lactated ringers, dextrose, sucrose, and mannitol, aqueporin receptors modulating agents, agonists or antagonists, Hg Cl2, G-protein modulating agents, tolvaptan, convivaptan, and vaptans, and
 (v) a hormone selected from the group consisting of cortisol, estradiol, progesterone, medroxyprogesterone, insulin, glucagon, thyroid hormone, and aldosterone,
 wherein the exogenous physical force provides a shear stress of about 200 dynes/cm² or greater, the method further comprising using a circulatory assist device to pump blood in a patient's body, wherein the circulatory assist device provides the exogenous physical force.

10. The method of claim 9, wherein the lipid or lipid related compound is selected from the group consisting of fatty acids, glycerolipids, glycerophospholipids, sphingolipids, saccharolipids, polyketides, sterol lipid, and prenol lipid.

11. The composition of claim 9, wherein the agent is non-atherogenic cholesterol or DMSO.

12. The method of claim 9, wherein the cells comprise one or more of platelets, red blood cells, white blood cells, and circulating precursor and stem cells, and wherein the composition is applied to the cells.

13. The method of claim 9, wherein the force provides a shear stress of between 200 dynes/cm² to about 1,000 dynes/cm².

14. The method of claim 9, wherein the force provides a shear stress of up to about 1,000 dynes/cm².

15. The method of claim 13, wherein the agent is selected from the group consisting of DMSO, non-atherogenic cholesterol, and taxel.

16. The method of claim 9, wherein the circulatory assist device is a VAD.

* * * * *